(12) United States Patent
Dariani et al.

(10) Patent No.: US 6,602,887 B2
(45) Date of Patent: **\*Aug. 5, 2003**

(54) CHRONIC, BOLUS ADMINISTRATION OF D-THREO METHYLPHENIDATE

(75) Inventors: Maghsoud M. Dariani, Fanwood, NJ (US); Andrew L. Zeitlin, Millington, NJ (US); Jerome B. Zeldis, Princeton, NJ (US)

(73) Assignee: Celegene Corporation, Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/864,617

(22) Filed: May 24, 2001

(65) Prior Publication Data

US 2001/0041717 A1 Nov. 15, 2001

Related U.S. Application Data

(60) Division of application No. 09/337,310, filed on Jun. 21, 1999, now Pat. No. 6,255,325, which is a division of application No. 08/937,684, filed on Sep. 29, 1997, now Pat. No. 5,922,736, which is a continuation-in-part of application No. 08/827,230, filed on Apr. 2, 1997, now Pat. No. 5,908,850, which is a continuation of application No. 08/567,131, filed on Dec. 4, 1995, now abandoned, and a continuation of application No. 08/647,642, filed on May 15, 1996, now abandoned, which is a continuation-in-part of application No. 08/583,317, filed on Jan. 5, 1996, now Pat. No. 5,733,756, and a continuation-in-part of application No. 08/567,131.

(51) Int. Cl.[7] ............................................. A61K 31/445
(52) U.S. Cl. ...................................................... 514/317
(58) Field of Search .......................................... 514/317

(56) References Cited

U.S. PATENT DOCUMENTS

| | | | |
|---|---|---|---|
| 2,507,631 A | 5/1950 | Hartmann et al. | 260/294 |
| 2,957,880 A | 10/1960 | Rometsch | 546/233 |
| 4,992,445 A | 2/1991 | Lawter et al. | 514/279 |
| 5,104,899 A | 4/1992 | Young et al. | 514/646 |
| 5,114,946 A | 5/1992 | Lawter et al. | 514/279 |
| 5,217,718 A | 6/1993 | Colley et al. | 424/449 |
| 5,283,193 A | 2/1994 | Yamamoto et al. | 435/280 |
| 5,284,769 A | 2/1994 | Evans et al. | 435/280 |
| 5,331,000 A | 7/1994 | Young et al. | 514/570 |
| 5,362,755 A | 11/1994 | Barberich et al. | 514/649 |
| 5,375,693 A | 12/1994 | Woosley et al. | 514/317 |
| 5,449,743 A | 9/1995 | Kobayashi et al. | 528/355 |
| 5,733,478 A | 3/1998 | Creech et al. | 252/400.21 |
| 5,733,756 A | 3/1998 | Zeitlin et al. | 435/122 |
| 5,837,284 A | * 11/1998 | Mehta et al. | |
| 5,908,850 A | * 6/1999 | Zeitlin et al. | 514/315 |
| 5,922,736 A | * 7/1999 | Dariani et al. | |
| 6,255,325 B1 | * 7/2001 | Dariani et al. | 514/317 |

FOREIGN PATENT DOCUMENTS

| | | | |
|---|---|---|---|
| WO | WO 97/03671 | * | 2/1997 |
| WO | WO 97/03672 | * | 2/1997 |
| WO | WO 97/03673 | * | 2/1997 |
| WO | WO 98/23263 | | 6/1998 |

OTHER PUBLICATIONS

Angrist et al., *J. Clin. Psychopharm.*, 1992, 12(4), 268–272.
Barkley et al., *Pediatrics*, 1990, 86(2), 184–192.
Barkley et al., *Pediatrics*, 1991, 87(4), 519–531.
Golinko, *Prog. Neuro-Psychopharmacol. Biol. Psychiat.*, 1984, 8, 1–8.
Greenhill, "Pharmacologic Treatment of Attention Deficit Hyperactivity Disorder", *Pediatric Psychopharmacology*, 1992, 15(1), 1–27.
Holmes et al., "Psychostimulant response in Aids-Related complex patients" *J. Clin. Psychiatry*, 1989, 50(1), 5–8, Biosis Abstract No. 87129969.
Scott, "Stereoisomers and Drug Toxicity", *Drug Safety*, 1993, 8(2), 149–159.
Srinivas et al., "Enantioselective pharmacolinetics and pharmacodynamics of racemic threo-methylphenidate in children with attention deficit hyperactivity disorder" *Clin. Pharmacol. Ther.*, 1992, 52(5), 561–568, Biosis Abstract No. 95066168.
White et al Mehylphenidate as a Treatment for Depression in Acquired Immunodeficiency Syndrome: An n–of–1 Trial, *J. Clin. Psychiatry*, 1992, 53(5), 153–156.
Aoyama et al., "Pharmacolinetics and pharmacodynamics of (+)-threo-methylphenidate enantiomer in patients with hypersomnia", *Clin. Pharmacol. Ther.*, 1994, 55(3), 270–276.
Bowden et al., "Reactions of Carbonyl Compounds in Basic Solutions the Alkaline Hydrolysis of N–Methyl, N–Phenyl, and Bicyclo Lactams Penicillins, and N–Alkyl–N–methylacetamides", *J. Chem. Soc. Perkin Trans.*, 1990, 12, 2111–2116.
Brown G., "The Use of Methylphenidate for Cognitive Decline Associated with HIV Disease", *Int'l J. Psychiatry Med.*, 1995, 25(1), 21–37.
Brown, "Pharmacological Action and Drug Development", *Chirality in Drug Design and Synthesis*, Academic Press Inc., 1990, 4–7.
Corey et al., "A New Synthetic Approach to the Penicillins", *J. Am. Chem. Soc.*, 1965, 87(11), 2518–2519.
Ding et al., Cis- and trans-Axetidin-2-ones from Nitrones and Copper Acetylide, *J. Chem. Soc. Perkin*, 1976, 22, 2382–2386.

(List continued on next page.)

Primary Examiner—Raymond Henley, III
(74) *Attorney, Agent, or Firm*—Woodcock Washburn LLP

(57) ABSTRACT

Chronic bolus administration of D-threo methylphenidate is provided. The administration of the D-threo isomer eliminates adverse side effects associated with the DL racemate, and provides improved effectiveness. The compositions and methods of the invention are useful in treating nervous system disorders including attention deficit disorder, attention deficit hyperactivity disorder, and cognitive decline associated with systemic diseases such as acquired immunodeficiency syndrome.

8 Claims, No Drawings

OTHER PUBLICATIONS

Douzenis et al., "Phychiatric Disorder in HIV Disease: Description of 200 Referrals to a Liaison psychiatry Service", *Proc. 7th. Int'l Conf. AIDS*, 1991, 215 (M.B.2135–Summary).

Earle et al., "Synthesis and Hydrolysis of some Fused–ring β–Lactams", *J. Chem. Soc.*, 1969, 2093–2098.

Greenhill L., "Attention–Deficit Hyperactivity Disorder", *Child & Adol. Psych. Clin. N.A.*, 1995, 4(1), 123–168.

Hou, J.P. et al., "Beta–Lactam Antibiotics: Their Physiochemical Properties and Biological Activities in Relation to Structure", *J. Pharm. Sci.*, 1971, 60(4), 503–532.

Klibanov, "Asymmetric Transformations Catalyzed by Enzymes in Organic Solvents", *Acc. Chem. Res.*, 1990, 23, 114–120.

Moll F., "Darstellung von 1–Aza–bicyclo[4.2.0]octan–2–on", *Naturforsch Teil B.*, 1966, 21, 297.

Navia et al., "The AIDS Dementia Complex: I. Clinical Features", *Annals of Neurology*, 1986, 19, 517–524.

Patrick et al., "Pharmacology of the Enantiomers of threo–Methylphenidate", *J. Pharmacol & Exp. Terhap.*, 1987, 241, 152–158.

Rieder et al., "Diagnosis of Sulfonamide Hypersensitivity Reactions by In–Vitro "Rechallenge" with Hydroxylamine Metabolites", *Ann. Intern Med.*, 1989, 110, 286–289.

Srinivas et al., "Enantioselective Pharmacokinetics of dl–threo–Methylphenidate in Humans", *Pharmacol Res.*, 1993, 10(1), 14–21.

Srinivas et al., "Enantiomeric Gas Chromatography Assay with Electron Capture Detection for d–Ritalinic Acid in Plasma", *J. Chromatagraph*, 1990, 530, 327–336.

Srinivas et al., "Sterioselective Disposition of Methylphenidate in Children with Attention Deficit Disorder", *J. Pharmacol. Exp. Ther.*, 1987, 241(1), 300–306.

Staal et al., "Glutathione deficiency and human immunodeficiency virus infection", *Lancet*, 1992, 339, 909–912.

Uetrecht et al., "Idiosyncratic Drug Reactions: Possible Role of Reactive Metabolites Generated by Leukocytes", *Pharmacol Res.*, 1989, 6(4), 265–273.

* cited by examiner

CHRONIC, BOLUS ADMINISTRATION OF D-THREO METHYLPHENIDATE

This patent application is divisional application of application Ser. No. 09/337,310, filed Jun. 21, 1999, now U.S. Pat. No. 6,255,325, which is a divisional of application Ser. No. 08/937,684, filed Sep. 29, 1997, now U.S. Pat. No. 5,922,736, which is a continuation-in-part of application Ser. No. 08/827,230, filed Apr. 2, 1997, now U.S. Pat. No. 5,908,850, and of application Ser. No. 08/647,642, filed May 15, 1996, now abandoned; which is a continuation-in-part of application Ser. No. 08/583,317, filed Jan. 5, 1996, now U.S. Pat. No. 5,773,756; and of application Ser. No. 08/567,131, filed Dec. 4, 1995, now abandoned.

FIELD OF THE INVENTION

The present invention is directed to methods and compositions for treating nervous system disorders such as attention deficit disorder, attention deficit hyperactivity disorder, cognitive decline associated with acquired immunodeficiency syndrome, and similar conditions. The methods involve the administration of a single, bolus dose of a composition comprising D-threo methylphenidate. The compositions are substantially free of L-threo methylphenidate and of erythro forms of methylphenidate.

BACKGROUND OF THE INVENTION

Attention Deficit Disorder (ADD), a commonly diagnosed nervous system illness in children, is generally treated with methylphenidate hydrochloride (available commercially as, e.g., Ritalin®). Symptoms of ADD include distractibility and impulsivity. A related disorder, termed Attention Deficit Hyperactivity Disorder (ADHD), is further characterized by symptoms of hyperactivity, and is also treated with methylphenidate hydrochloride. Methylphenidate drugs have also been used to treat cognitive decline in patients with Acquired Immunodeficiency Syndrome (AIDS) or AIDS related conditions. See, e.g., Brown, G., Intl. J. Psych. Med. 25(1): 21–37 (1995); Holmes et al., J. Clin. Psychiatry 50: 5–8 (1989).

Methylphenidate exists as four separate optical isomers as follows:

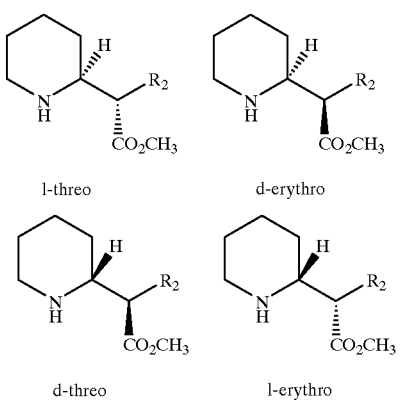

l-threo     d-erythro d-threo     l-erythro wherein $R_2$ is phenyl. Pharmaceutically acceptable salts are generally administered clinically. Other phenidate drugs, which also can be administered according to the invention, include those in which the methyl group in the above structures is replaced by $C_2$–$C_4$ alkyl and those in which $R_2$ is optionally substituted with $C_1$–$C_4$ alkyl.

Clinically, the threo pair of enantiomers of methylphenidate hydrochloride is generally administered for the treatment of ADD and ADHD. The hydrochloride salt is commonly referred to simply as "methylphenidate". Unless indicated otherwise, the term "methylphenidate" is used broadly herein to include methylphenidate and pharmaceutically acceptable salts thereof, including methylphenidate hydrochloride.

The threo racemate (pair of enantiomers) of methylphenidate is a mild central nervous system stimulant with pharmacological activity qualitatively similar to that of amphetamines. Undesirable side effects associated with the use of the DL-threo racemate of methylphenidate include anorexia, weight loss, insomnia, dizziness and dysphoria. Furthermore, the racemate, which is a Schedule II controlled substance, produces a euphoric effect when administered intravenously or through inhalation or ingestion, and thus carries a high potential for abuse.

Srinivas et al. studied the administration of DL-threo-, D-threo, and L-threo-methylphenidate to children suffering from ADHD, and reported that the pharmacodynamic activity of DL-threo-methylphenidate resides in the D-threo isomer (Clin. Pharmacol. Ther., 52: 561–568 (1992)). While DL-threo-methylphenidate is generally used therapeutically, this racemate includes the L isomer which apparently makes no significant contribution to the pharmacological effectiveness of the drug. The removal of the L isomer is expensive, however, and there has been no reason to do so.

An additional problem is that, generally, children being treated with dl-threo methylphenidate must take one or more doses during the day in order to receive optimal benefit from the treatment. This creates a problem for school administrators who must store a controlled substance on school premises, with the associated risk that it may be stolen for illicit use. Furthermore, children may be traumatized by ridicule from peers when they must take medication at school.

Sustained release formulations of DL-threo methylphenidate have been developed, which provide for slow release of the drug over the course of the day. However, it has been observed that peak plasma concentrations of the drug are lower when sustained release formulations are used as compared to conventional dosage forms administered throughout the day. In some studies, sustained release formulations of DL-threo methylphenidate have been shown to have lower efficacy than conventional dosage forms.

Pulsed-release dosage forms, wherein a single dosage form contains two doses, one of which is released shortly after ingestion and the other of which is released following a delay of several hours, have recently been proposed as a method for administering a maximally effective dose regime. While pulsed dosage forms provide for efficient release of multiple doses of medication at predetermined intervals, such dosage forms can be complex and expensive to manufacture. Furthermore, while pulsed-release dosage forms are suitable for administration of medications such as methyl phenidate to children, multiple releases of the medication are not required for all patients. However, it is desirable to administer to all patients the most effective and efficient dosage of mediation and, in the case of methyl phenidate, it is now believed that this end is best achieved by administering the single, effective isomer, i.e. D-threo methylphenidate.

While the D-threo isomer of methylphenidate has been shown to be the pharmacodynamically active isomer, the administration of the single isomer has been neither studied nor administered clinically on a chronic basis. Thus, the effects of administering a single isomer on a chronic basis as compared to the conventionally administered racemate have not heretofore been recognized or understood.

There remains a need for methods for delivering methylphenidate with maximum effectiveness and minimal potential for abuse. Furthermore, there is a need for a dosage form which provides, in a single administration, a patient's daily dose requirement of optimally effective methylphenidate, eliminating the need to take a second dose, while minimizing undesirable side effects and maximizing ease of administration.

SUMMARY OF THE INVENTION

The present invention provides, in one aspect, a method for treating at least one of the following disorders: attention deficit disorder (ADD), attention deficit hyperactivity disorder (ADD), or AIDS-related dementia. The method involves the chronic administration of D-threo-methylphenidate or a pharmaceutically acceptable salt thereof, substantially free of both L-threo-methylphenidate and erythro methylphenidates. It is now believed that the L isomer likely contributes to the side effects associated with the commercial drug. It is thus desirable to administer only the active D-threo form of the drug. The D-threo methylphenidate is administered in single, bolus dosages, with one dose being administered in each twenty-four hour period.

Another aspect of the present invention provides pharmaceutical compositions for treating a nervous system disorder in a patient needing treatment, comprising a bolus dosage form of D-threo-methylphenidate or a pharmaceutically acceptable salt thereof, in an amount sufficient for daily effectiveness, which dosage is substantially free of both L-threo-methylphenidate and erythro methylphenidates. The administration of only the pharmacodynamically active D-threo form of methylphenidate can provide efficacious treatment for an entire day without undesirable side effects such as interference with patient sleep patterns or anoretic behavior. It has been surprisingly and unexpectedly discovered that the beneficial effects of the D-threo isomer persist for a longer period time when the D-threo isomer is administered alone than when it is administered in combination with the L-threo isomer.

While it is not intended that the present invention be bound by any particular theory, it is believed that the L isomer functions as an antagonist to the D isomer. Thus, another aspect of the present invention provides methods for ameliorating or counteracting the effects of methylphenidate drugs, comprising administering L-threo methylphenidate to a patient who has a serum level of D-threo methylphenidate.

The present inventors have observed that 6 to 8 hours following administration of DL-threo methylphenidate, D-threo methylphenidate, or a placebo, patients who were given the D-threo isomer free of the L isomer performed better in objective tests than patients who received the DL-threo racemate or a placebo. In contrast, the patients who received DL-threo racemate did not perform better after that time period than those who received a placebo. Furthermore, subjective observations of the same patients indicated that those who received only the D-threo isomer experienced beneficial effects of the drug for longer times than did those who received the DL-threo racemate. Accordingly, it is now believed that the bolus administration of D-threo methylphenidate can give rise to beneficial effects for far longer than administration of the racemate. Moreover, it is now possible for these effects to last for entire working or school days following administration of a bolus dose on a chronic basis.

It is expected that D-threo methylphenidate will be particularly useful in treating patients affected by ADD when who must function in a structured environment such as school or work. Any formulation which provides a dosage sufficient to provide from about 6 to about 8 hours of efficacy should allow an ADD-affected individual to function in a structured environment without having to take another dose during the day.

According to one method of the present invention, bolus dosage forms are administered of D-threo methylphenidate substantially free of L-threo methylphenidate and of erythro methylphenidates. "Substantially free", as used herein, means that the dosage forms comprise at least about 95 percent, preferably at least about 97 percent, and more preferably at least about 99 percent of the D-threo isomer, to the exclusion of the L-threo and erythro forms. The D-threo form can be isolated by methods known to those skilled in the art.

"Chronic", as used herein, refers to continuous, regular, long-term therapeutic administration, i.e. periodic administration without substantial interruption, such as, for example, daily, for a time period of at least several weeks or months to several years, for the purpose of treating a nervous disorder in a patient needing treatment.

"Bolus", as used herein, refers to administration of a drug as a single event. The term "bolus" is intended to exclude dosage forms such as sustained release, pulsed release, and time release, and includes any dosage form which can be used to deliver a single dose. According to the present invention, a bolus is preferably administered to a patient in need of treatment once daily, more preferably in the morning. The bolus dosages of the present invention may be administered in any conventional form known to those skilled in the art. Suitable methods for administration include oral dosage forms, injection, and infusion.

For pharmaceutical use, the compounds described herein may be taken up in pharmaceutically acceptable carriers, such as, for example, solutions, suspensions, tablets, capsules, ointments, elixirs and injectable compositions. Pharmaceutical preparations generally can contain from about 1% to about 90% by weight of active ingredient. Preparations which are in single dose form, "unit dosage form", preferably contain from about 20% to about 90% active ingredient. As used herein, the term "active ingredient" refers to compounds described herein, salts thereof, and mixtures of compounds described herein with other pharmaceutically active compounds. Dosage unit forms such as, for example, tablets or capsules, typically contain from about 0.001 to about 1.0 g of active ingredient. Pharmaceutical preparations may be administered orally, parenterally, or topically.

Pharmaceutical preparations containing compounds described herein may be prepared by methods known to those skilled in the art, such as, for example, conventional mixing, granulating, dissolving, or lyophilizing. Oral dosage forms include capsules, pills, tablets, troches, lozenges, melts, powders, solutions, suspensions and emulsions. The oral dosage forms provided by the invention can be in the form of tablets, caplets, and the like and can be of any shape suitable for oral administration of a drug, such as spheroidal, cube-shaped, oval, bean shaped, or ellipsoidal. For oral dosage forms, for example, the compounds may be combined with one or more solid pharmaceutically acceptable carriers, optionally granulating the resulting mixture. Pharmaceutically acceptable adjuvants may optionally be included, such as, for example, flow-regulating agents and lubricants. Suitable carriers include, for example, fillers such as sugars, cellulose preparations, calcium phosphates; and binders such as methylcellulose, hydroxymethylcellulose, and starches, such as, for example, maize starch, potato starch, rice starch, and wheat starch. The dosage form may be in the form of granules, which may be irregularly shaped. The dosage form can comprise a capsule containing particles. Examples of orally administrable pharmaceutical preparations are dry-filled capsules consisting of gelatin, and soft sealed capsules consisting of gelatin and a plasticizer such as glycerol or sorbitol. The dry-filled capsules may contain the active ingredient in the form of a granulate, for example in admixture with fillers, binders, glidants, and stabilizers. In soft capsules, the active ingredient is preferably dissolved or suspended in a suitable liquid adjuvant, such as, for example, a fatty oil, paraffin oil, or liquid polyethylene glycol, optionally in the presence of stabilizers. Other oral administrable forms include syrups containing active ingredient, for example, in suspended form at a concentration of from about 0.01% to 20%, or in a similar concentration that provides a suitable single dose when administered, for example, in measures of from about 2 to about 5 milliliters. Suitable excipients for use in oral liquid dosage forms include diluents such as water and alcohols, for example ethanol, benzyl alcohol and polyethylene alcohols, either with or without the addition of a pharmaceutically acceptable surfactant, suspending agent, or emulsifying agent. Also suitable are powdered or liquid concentrates for combining with liquids such as milk. Such concentrates may also be packed in single dose quantities.

The compounds described herein may be administered parenterally, that is, subcutaneously, intravenously, intramuscularly, or interperitoneally, as injectable dosages of the compound in a physiologically acceptable diluent with a pharmaceutical carrier. Solutions for parenteral administration may be in the form of infusion solutions. A pharmaceutical carrier may be, for example, a sterile liquid or mixture of liquids such as water, saline, aqueous dextrose and related sugar solutions, an alcohol such as ethanol, glycols such as propylene glycol or polyethylene glycol, glycerol ketals such as 2,2-dimethyl-1,3-dioxolane-4-methanol, ethers such as poly(ethyleneglycol)400, oils, fatty acids, fatty acid esters or glycerides, with or without the addition of a pharmaceutically acceptable surfactant such as a soap or detergent, suspending agent such as pectin, carbomers, methylcellulose, hydroxypropylmethylcellulose, or carboxymethylcellulose, or emulsifying agent or other pharmaceutically acceptable adjuvants. Examples of oils which may be used in parenteral formulations include petroleum, animal, vegetable, or synthetic oils such as, for example, peanut oil, soybean oil, sesame oil, cottonseed oil, corn oil, olive oil, petrolatum, and mineral oil. Suitable fatty acids include, for example, oleic acid, stearic acid, and isostearic acid. Suitable fatty acid esters include ethyl oleate and isopropyl myristate. Suitable soaps include alkaline metal, ammonium and triethanolamine salts of fatty acids. Suitable detergents include cationic detergents such as dimethyl dialkyl ammonium halides and alkyl pyridinium halides; anionic detergents such as alkyl, aryl and olefin sulfonates, monoglyceride sulfates and sulfosuccinates; nonionic detergents such as fatty amine oxides, fatty acid alkanolamides and polyoxyethylenepropylene copolymers; and amphoteric detergents such as alkyl-(-aminopropionates and 2-alkylimidazoline quaternary ammonium salts; as well as mixtures of detergents. Parenteral preparations will typically contain at least about 0.01% by weight of active ingredient in solution. Preservatives and buffers may also be used advantageously. Injection suspensions may include viscosity-increasing substances such as, for example, sodium carboxymethylcellulose, sorbitol or dextran, and may also include stabilizers. In order to minimize irritation at the site of injection, injectable compositions may contain a non-ionic surfactant having a hydrophile-lipophile balance (HLB) of from about 12 to about 17. The quantity of surfactant in such formulations ranges from about 5% to about 15% by weight. The surfactant may be a single component having the above HLB or a mixture of two or more components having the desired HLB. Particular examples of useful surfactants include polyethylene sorbitan fatty acid esters, such as, for example, sorbitan monooleate.

The preferred quantity of D-threo methylphenidate to be used in a dosage for treating a particular patient can be readily determined by one skilled in the art. Factors determining the appropriate dosage include the weight and age of the patient, the type and extent of the disorder being treated, and other conditions of the patient including other disorders and other medications, if any, that the patient is taking. Generally, the dosage of D-threo methylphenidate will be from about 0.01 mg/kg of patient body weight to about 1 mg/kg of patient body weight. Appropriate quantities can be determined by one skilled in the art. For example, a relatively small child will generally require a dose of from about 0.03 to about 0.3 mg/kg, while a larger child or an adult may require a dose of from about 0.1 mg/kg to about 0.4 or 0.5 mg/kg.

A physician treating a patient with ADD will generally titrate the dose of methylphenidate until the desired therapeutic effects is achieved. For example, a patient with ADD will start by taking 2.5 mg of d-MPH approximately 30 to 60 minutes before beginning school or work. If the patient's behavior is not well-controlled by this dose after two or three days and the patient has not experienced "incapacitating" anxiety, the dose will be raised to 5 mg. After two days, a lack of therapeutic effect will necessitate increasing the dose to 10 mg or higher safe doses. Once a dose of d-MPH is determined to be effective, this dose will remain stable unless the child is growing. It is not unusual for the dose of methylphenidate that was effective in a 7 year old to be increased when the child becomes 9 or 10 years old.

On the other hand, most teenagers can achieve appropriate effectiveness from a particular dose for many years.

Response by patients with ADD or ADHD is generally determined by two types of measurements: objective measures of a patient's ability to concentrate and remain focused on a task such as performing a math test; and subjective scores of a patient's performance. The inventors have discovered that children who had been treated with racemic methylphenidate (DL-threo methylphenidate) showed significantly better responses when treated with a formulation containing only the D enantiomer. Furthermore, it has been surprisingly observed that the beneficial effects of administration of the D-enantiomer alone, when measured by both objective and subjective tests, persisted for a significantly longer time than when the same patients were treated with the racemic mixture.

The following examples are merely illustrative of the present invention and should not be considered limiting of the scope of the invention in any way. These examples and equivalents thereof will become more apparent to those skilled in the art in light of the present disclosure and the accompanying claims.

EXAMPLE 1

Double Blind, Randomized Patient Study

A total of 35 children aged 9 to 12 years with ADHD (of which 31 were evaluable) were enrolled, at three sites, in a double-blind, randomized, placebo-controlled, crossover study consisting of nine consecutive weekly visits (i.e., a total of nine weeks duration). At each visit, serial blood samples were taken for pharmacokinetic analysis. A battery of safety and pharmacodynamic measurements were performed.

At Visit 1 (which served as the baseline visit), all subjects were given a placebo in a single-blind manner. For Visits 2–8, subjects received one of two treatment regimens and a placebo in a double blind, randomized manner. The randomization occurred within each treatment regimen. One group of subjects received three single doses of DL methylphenidate (DL-MPH) and then, at the crossover, received three single doses of D-MPH; while the other group received three single doses of D-MPH followed by three single doses of DL-MPH. The placebo was given at one of the visits within either treatment regimen. The D-MPH was provided in capsules of 2.5, 5, and 10 mg. The DL-MPH was matched and provided in capsules of 5, 10, and 20 mg, accounting for the equimolar presence of two isomers. A matching placebo was also provided. All capsules were administered orally.

At Visit 9, subjects were randomly given one of the treatments unless they had missed a study visit. In that case, Visit 9 was used to repeat the missed study visit. A minimum of six days separated each of the 9 visits, during which time subjects received their standard medication.

Mean Plasma Concentration

D-MPH and DL-MPH were found to have equivalent pharmacokinetics and safety profiles, and resulted in no serious adverse effects. The amount of D-MPH delivered by a 2.5 mg dose of ONLY D-MPH is approximately equal to the amount of D-MPH delivered by the 5 mg close of racemic DL-MPH. Similarly, a 5 mg dose of only D-MPH provides the same amount of the D isomer as a 10 mg dose of the racemic DL mixture. Below are listed the mean plasma concentrations of D-MPH as determined 4, 6, and 8 hours after Ingestion.

TABLE 1

Mean plasma concentration, nanograms per milliliter (ng/ml) of D-MPH after ingesting D-MPH or DL-MPH.

| Formulation | 4 hours | 6 hours | 8 hours |
|---|---|---|---|
| 2.5 mg D-MPH | 3.00 | 1.82 | 0.67 |
| 5 mg DL-MPH | 2.94 | 1.91 | 0.85 |
| 5 mg D-MPH | 5.86 | 3.75 | 1.84 |
| 10 mg DL-MPH | 7.66 | 5.20 | 2.66 |
| 10 mg D-MPH | 11.73 | 7.65 | 3.81 |
| 20 mg DL-MPH | 12.50 | 8.15 | 3.85 |

Objective Measure: Math Test

A computerized math test provided a measure of attention, concentration and work output. This test was administered 30 minutes before, and 4 hours, 6 hours, and 8 hours after medication administration. Table 2 lists statistical significance (p values) for comparisons between test results obtained after administration of D-MPH or DL-MPH and test results obtained after administration of a placebo. Similar notation is used in other data tables below. Data in Table 2 were obtained 30 minutes before, and at 4, 6, and 8 hours after, administration.

Four hours following administration, 10 mg of the D isomer was as effective as 20 mg of the DL racemate, as measured by improvement on the math test. The effectiveness as measured by improvement on the math test was evident only with 10 mg D-MPH 6 and 8 hours after administration of medication, and not with its equivalent dose as contained within 20 mg of DL-MPH. Superiority in effectiveness over the placebo was not observed with doses of D-MPH of less than 10 mg, and no significant effect was observed with even twice the dose of racemic DL-MPH beyond 4 hours. At 6 hours and 8 hours after administration, superiority over placebo was not achieved with lower doses than 10 mg of D-MPD or with any dose of DL-MPH used in this study.

TABLE 2

P values of the comparisons of math scores achieved at various time intervals after taking placebo, with math scores achieved after taking 20 mg DL-threo methylphenidate or 10 mg D-threo methylphenidate.

| | Test 1 (−30 mm) | Test 4 (4 hours) | Test 5 (6 hours) | Test 6 (8 hours) |
|---|---|---|---|---|
| placebo - DL 20 mg | NS* | <0.001 | NS | NS |
| placebo - D 10 mg | NS | <0.001 | <0.001 | 0.289 |

*NS, here and below, indicates no statistically significant difference. If results of comparison are statistically significant (p < 0.05), the p value is listed.

Connors, Loney, and Milich (CLAM) Rating

The CLAM Rating Scale is a standard, subjective measure of inattention, overactivity, aggression, and defiance. Rating was completed 6 hours after drug administration by observers who were blind as to which study medication each subject received. The scale contains 16 items:
1. Restless or Overactive
2. Disturbs other children
3. Mood changes quickly and dramatically
4. Cries often and easily
5. Demands must be met immediately
6. Teases other children and interferes with their activities
7. Fidgeting
8. Hums
9. Excitable, impulsive
10. Inattentive, easily distracted
11. Fails to finish things started
12. Quarrelsome
13. Acts smart
14. Temper outbursts
15. Defiant
16. Uncooperative While all three doses of D-MPH significantly reduced the overall CLAM score, indicating clinical benefit over the placebo, only the 10 mg and 20 mg doses of DL-MPH remained effective six hours after drug administration.

TABLE 3

P values for comparison of overall CLAM scores 6 hours after administration of D-MPH or DL-MPH, with overall CLAM scores 6 hours after administration of placebo

| placebo-DL 5 mg | NS* | placebo-D 2.5 mg | 0.0065 |
|---|---|---|---|
| placebo-DL 10 mg | 0.216 | placebo-D 5 mg | <0.001 |
| placebo-DL 20 mg | <0.001 | placebo-D 10 mg | <.001 |

*NS, no significant difference; if statistically significant (p < 0.05), the p value is listed.

Two subscales were calculated from the CLAM: the aggression/defiance (A/D) subscale and the inattention/overactivity (I/O) subscale. All doses of D-MPH were superior to the placebo using the A/D subscale. However, only the highest dose (20 mg) of DL-MPH was superior to placebo for the AID subscale. The highest doses of both the D-MPH and DL-MPH formulations were superior to the placebo in the I/O subscale. While the 5 mg dose of D-MPH was also superior to the placebo, the equivalent as administered in a 10 mg dose Of DL-MPH was not.

Shown below are p values for the comparisons of scores on the two CLAM subscales obtained 6 hours after administration of DL or D-MPH with scores obtained 6 hours after administration of a placebo.

TABLES 4 and 5

Comparison of scores on CLAM subscales 6 hours after administration of DL or D-MPH or a placebo.

Aggression-Defiance (A/D) Score

| | | | |
|---|---|---|---|
| placebo-DL 5 mg | NS | placebo-D 2.5 mg | 0.0279 |
| placebo-DL 10 mg | NS | placebo-D 5 mg | <0.001 |
| placebo-DL 20 mg | <0.001 | placebo-D 10 mg | <.001 |

Inattention-Over-activity (I/O) Score

| | | | |
|---|---|---|---|
| placebo-DL 5 mg | NS | placebo-D 2.5 mg | NS |
| placebo-DL 10 mg | NS | placebo-D 5 mg | <0.0097 |
| placebo-DL 20 mg | <0.001 | placebo-D 10 mg | <0.001 |

Scores for the individual behaviors were also determined. According to several observed individual behaviors (fidgeting, quarrelsome and defiant), 2.5 mg D-MPH was determined to provide efficacy superior to that of a placebo, but 5 mg of DL-MPH was not similarly effective. Also, 5 mg D-MPH provided efficacy superior to that of a placebo while 10 mg of DL-MPH did not, for the following behaviors: disturbs, demands, fidgeting, excitable, inattentive, and defiant.

For two behaviors, quarrelsome and acts smart, 10 mg d-MPH provided efficacy superior to that of the placebo while 20 mg of DL-MPH did not.

Results for individual behaviors are summarized below. Shown in the tables are p values for the comparisons of the results of individual behavior rating as obtained 6 hours after administration of D-MPH and DL-MPH to the results obtained 6 hours after administration of a placebo.

TABLES 6–13

P values for comparison of effectiveness of D-MPH and DL-MPH with that of placebo, as indicated by individual behaviors.

Disturbs

| | | | |
|---|---|---|---|
| placebo-dl 5 mg | NS | placebo-d 2.5 mg | NS |
| placebo-dl 10 mg | NS | placebo-d 5 mg | <0.0280 |
| placebo-dl 20 mg | <0.001 | placebo-d 10 mg | <0.001 |

Demands

| | | | |
|---|---|---|---|
| placebo-dl 5 mg | NS | placebo-d 2.5 mg | NS |
| placebo-dl 10 mg | NS | placebo-d 5 mg | 0.494 |
| placebo-dl 20 mg | 0.0335* | placebo-d 10 mg | 0.0011 |

Fidgeting

| | | | |
|---|---|---|---|
| placebo-dl 5 mg | NS | placebo-d 2.5 mg | 0.0360 |
| placebo-dl 10 mg | NS | placebo-d 5 mg | 0.0067 |
| placebo-dl 20 mg | <0.001 | placebo-d 10 mg | <0.001 |

Excitable

| | | | |
|---|---|---|---|
| placebo-dl 5 mg | NS | placebo-d 2.5 mg | NS |
| placebo-dl 10 mg | NS | placebo-d 5 mg | 0.494 |
| placebo-dl 20 mg | 0.0014 | placebo-d 10 mg | 0.001 |

Inattentive

| | | | |
|---|---|---|---|
| placebo-dl 5 mg | NS | placebo-d 2.5 mg | NS |
| placebo-dl 10 mg | NS | placebo-d 5 mg | 0.0149 |
| placebo-dl 20 mg | 0.0016 | placebo-d 10 mg | <0.001 |

Quarrelsome

| | | | |
|---|---|---|---|
| placebo-dl 5 mg | NS | placebo-d 2.5 mg | 0.0115 |
| placebo-dl 10 mg | NS | placebo-d 5 mg | NS |
| placebo-dl 20 mg | NS | placebo-d 10 mg | 0.0016 |

TABLES 6–13-continued

P values for comparison of effectiveness of D-MPH and DL-MPH with that of placebo, as indicated by individual behaviors.

Acts Smart

| | | | |
|---|---|---|---|
| placebo-dl 5 mg | NS | placebo-d 2.5 mg | NS |
| placebo-dl 10 mg | NS | placebo-d 5 mg | NS |
| placebo-dl 20 mg | NS | placebo-d 10 mg | 0.001 |

Defiant

| | | | |
|---|---|---|---|
| placebo-dl 5 mg | NS | placebo-d 2.5 mg | 0.0010 |
| placebo-dl 10 mg | 0.0038 | placebo-d 5 mg | 0.0166 |
| placebo-dl 20 mg | <0.001 | placebo-d 10 mg | <0.001 |

At a dose of 5 mg, the D isomer provided efficacy for at least 6 hours following administration, as compared to the DL racemate, which required a twice that dosage to provide 6 hours of efficacy. Even more significantly, a 2.5 mg dose of the D isomer provided efficacy in controlling several behaviors, while even twice the dose of the DL racemate was ineffective against the same behaviors. For two behaviors (fidgeting and quarrelsome), even four times the dose of the racemate, i.e. 10 mg, showed no statistically significant improvement over the placebo as compared to 2.5 mg of the D isomer.

In conclusion, the data show that, according to both objective and subjective measures, D-MPH was not only more effective than a placebo in controlling subjective behaviors and in improving objective performance on a math test, but clearly provided efficacy for a significantly longer period of time than did an equivalent dose of DL-MPH.

EXAMPLE 2

Exemplary D-MPH Formulations

| Ingredient | Formulation (mg/tablet) | | |
|---|---|---|---|
| | #1 | #2 | #3 |
| Formulations for 2.5 mg D-MPH | | | |
| Starch 1500, NF (pre-gelatinized starch) | 30.0 | 30.0 | 23.4 |
| Active Drug | 2.5 | 2.5 | 2.5 |
| D&C Yellow Lake #10 | 0.9 | 0.6 | 1.5 |
| Lactose Monohydrate, NF (flast flow #316) | 61.9 | 61.6 | 75.0 |
| Sodium Starch Glycolate, NF | 1.5 | 4.0 | 27.35 |
| Micro-crystalline Cellulose, NF | 42.7 | 50.0 | 30.0 |
| Magnesium Stearate, NF | 0.5 | 1.3 | 0.25 |
| Total Weight Per Tablet | 140 | 150 | 160 |
| Formulations for 5 mg D-MPH | | | |
| Starch 1500, NF (pre-gelatinized starch) | 30.0 | 30 | 23.4 |
| Active Drug | 5 | 5 | 5 |
| D&C Yellow Lake #10 | 0.9 | 0.6 | 1.5 |
| Lactose Monohydrate, NF (flast flow #316) | 59.4 | 61.6 | 72.5 |
| Sodium Starch Glycolate, NF | 1.5 | 4.0 | 27.35 |
| Micro-crystalline Cellulose, NF | 42.7 | 47.5 | 30.0 |
| Magnesium Stearate, NF | 0.5 | 1.3 | 0.25 |
| Total Weight Per Tablet | 140 | 150 | 160 |
| Formulations for 10 D-MPH | | | |
| Starch 1500, NF (pre-gelatinized starch) | 30.0 | 30.0 | 23.4 |
| Active Drug | 10 | 10 | 10 |
| D&C Yellow Lake #10 | 0.9 | 0.6 | 1.5 |
| Lactose Monohydrate, NF (flast flow #316) | 54.4 | 61.6 | 67.5 |

-continued

| Ingredient | Formulation (mg/tablet) | | |
|---|---|---|---|
| | #1 | #2 | #3 |
| Sodium Starch Glycolate, NF | 1.5 | 4.0 | 27.35 |
| Micro-crystalline Cellulose, NF | 42.7 | 42.5 | 30.0 |
| Magnesium Stearate, NF | 0.5 | 1.3 | 0.25 |
| Total Weight Per Tablet | 140 | 150 | 160 |

Various modifications of the invention, in addition to those described herein, will be apparent to those skilled in the art from the foregoing description. Such modifications are intended to fall within the scope of the appended claims.

What is claimed is:

1. A method of treating at least one of attention deficit disorder, attention deficit hyperactivity disorder, or AIDS-related dementia, comprising the chronic administration of a compound having the formula:

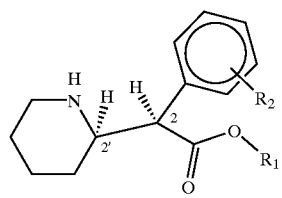

or a pharmaceutically acceptable salt thereof, wherein $R_1$ is $C_1$–$C_4$ alkyl, and $R_2$ is hydrogen or $C_1$–$C_4$ alkyl, substantially free of both l-threo and erythro forms thereof, said administration comprising a single, bolus dosage of said compound in each twenty-four hour period.

2. The method of claim 1 wherein said bolus dosage is administered orally.

3. The method of claim 1 wherein said bolus dosage is administered by injection or infusion.

4. The method of claim 1 wherein said dosage is administered each morning.

5. The method of claim 1 wherein said bolus dosage is from about 0.01 mg/kg to about 1 mg/kg of patient body weight.

6. The method of claim 1 wherein said bolus dosage is from about 0.1 mg/kg to about 0.5 mg/kg of patient body weight.

7. The method of claim 1 wherein said bolus dosage further comprises a pharmaceutically acceptable carrier.

8. The method of claim 1 wherein said chronic administration gives rise to efficacious treatment of the disorder without interfering with patient sleep patterns or engendering anoretic behavior.

* * * * *

UNITED STATES PATENT AND TRADEMARK OFFICE
CERTIFICATE OF CORRECTION

PATENT NO. : 6,602,887 B2  
DATED : August 5, 2003  
INVENTOR(S) : Dariani et al.

It is certified that error appears in the above-identified patent and that said Letters Patent is hereby corrected as shown below:

<u>Title page,</u>  
Item [73], Assignee, please delete "Celegene" and insert -- Celgene --.  
Item [60], Related U.S. Application Data, after "application No. 08/567,131" insert -- , now abandoned --.  
Item [56], References Cited, OTHER PUBLICATIONS, delete "Phychiatric" and insert therefor -- Psychiatric --.

<u>Column 6,</u>  
Line 11, delete "monooleate" and insert therefor -- monoöleate --.

<u>Column 8,</u>  
Line 3, delete "AID" and insert therefor -- A/D --.  
Line 15, in Table 2, delete "mm" and insert therefor -- min --.

Signed and Sealed this

Sixteenth Day of December, 2003

JAMES E. ROGAN  
*Director of the United States Patent and Trademark Office*